United States Patent [19]
Sakamoto et al.

[11] Patent Number: 4,735,945
[45] Date of Patent: Apr. 5, 1988

[54] METHOD FOR INHIBITING BONE RESORPTION AND COLLAGENASE RELEASE

[75] Inventors: Seizaburo Sakamoto; Masako Sakamoto, both of Chestnut Hill, Mass.

[73] Assignee: Vipont Laboratories, Inc., Fort Collins, Colo.

[21] Appl. No.: 839,229

[22] Filed: Mar. 13, 1986

[51] Int. Cl.⁴ ............................................ A61K 31/435
[52] U.S. Cl. ...................................... 514/279; 514/900
[58] Field of Search ............................... 514/279, 900

[56] References Cited

U.S. PATENT DOCUMENTS

| | | | |
|---|---|---|---|
| 4,256,743 | 3/1981 | Goldhaber | 514/900 |
| 4,406,881 | 9/1983 | Ladanyi | 424/145 |
| 4,517,172 | 5/1985 | Southard | 424/49 |
| 4,569,837 | 2/1986 | Suzuki et al. | 514/900 |
| 4,590,061 | 5/1986 | Southard | 424/49 |
| 4,599,228 | 7/1986 | Ladanyi | 424/52 |
| 4,683,133 | 7/1987 | Southard | 424/49 |

Primary Examiner—Douglas W. Robinson
Attorney, Agent, or Firm—Eric P. Schellin

[57] ABSTRACT

Method of inhibiting bone resorption and collagenase release in mammalian periodontal subjects using a benzo-c-phenanthridine alkaloid compound.

5 Claims, 5 Drawing Sheets

Culture Medium: 5.0 ml

Heparin-Sepharose 4B gel affinity chromatography
Tulip-shaped columns, gel bed: 0.8 x 2 cm
Eluted with 0.05 M Tris HCl buffer pH 7.6

Adsorbed:          Eluted: Serum Proteins

Eluted with 0.05 M Tris HCl buffer pH 7.6
containing 0.5 M Ca-acetate and 0.5 M NaCl Collagenase: 2.5 ml Desalted with PD-10 columns (Pharmacia Fine Chemicals)

Desalted Collagenase: 3.5 ml

Collagenase Assay

Substrate:    Reconstituted $^{14}C$-labeled collagen fibrils
(50 μl, 75 μg of collagen, total 3,000 cpm per assay)

Enzyme samples: 50–200 μl of desalted collagenase. Activation of
latent enzyme with 1 mM p-aminophenylmercuric acetate Incubation: For 6–20 h at 37°C

Fig. 1

METHOD FOR INHIBITING BONE RESORPTION AND COLLAGENASE RELEASE

FIELD OF THE INVENTION

The present invention relates to a method for controlling alveolar bone resorption in periodontal disease in mammals.

BACKGROUND OF THE INVENTION

Benzo-c-phenanthridine alkaloids can be extracted from plants of the families Papaveracease, Fumariaceae, and Berberidaceae. Some of the palnts of these familes include *Sanquinaria canadensis, Macleaya cordata, Bocconia frutescens, Carydalis sevctcozii, C. ledebouni, Argemone mexicanus,* and *Chelidonium majus.* Among the most important benzo-c-phenanthridine alkaloids obtained from these plants are sanguinarine, chelirubine, macarpine, allocryptopine, protopine, hemochelidonene, sanquilatine, sanguirubine, and chelerythrine.

The best known of these alkaloids is sanguinarine, which has been extracted from the *Sanguinaria canadensis* plant (otherwise known as bloodroot, teterwort, redroot, puccoon, etc) a perennial heb native to North America. The sanguinaria plant and its juices have been used for various purpsoes in pre-historic and historic times. The plants have been used, in particular, as a fold remedies. The plants have generally been used whole, either undried (fresh) or dired, and the usual procedure is to powder the dried plant and mix it with a carrier. This folk remedy has been tried for such conditions as asthma, bronchitis, dysenatry, ringworm, and a substantial list of other ailments.

The pure chemicals sanguinarine, chelerythrine, protopine, chelerubine, berberine, chelilutine, sanguilatine, macarpine, sanguirubine, and allocryptopine can be isolated from lants other than Sanguinaria. They are also available, although rarely, from some chemical supply houses. Semi-purified forms of the alkaloids are commercially available, and these are generally referred to as sanguinarine nitrate and sanguinarine sulfate. These "salts" are the salts of the mixed alkaloids of the plant Sanguinaria: mainly sanguinarine, chelerythrine, and protopine. While few references can be found in the literature regarding the usage of any of the pure benzo-phenanthridine alkaloids, plants containing such compounds have been used for a wide variety of medical ailments.

The alkaloid sanguinarine in solution has been shown to have some antifungal and antiprotozoan properties. The sanguinarine is applied as an emulsion topically to fungal infections. The antibacterial activity of sanguinarine has been found to vary with the attached radicals, and various salts of sanguinarine have been shown to have some activity. The hydrochloride and the sulfate salts have been found to have some activity against certain bacteria at certain concentrations. Sanguinarine nitrate is reported to have some bacteriostatic action against various types of bacteria.

The use of an extract of *Sanguinaria canadensis* as an ingredient in oral cleansing preparations, in particular, toothpaste, is disclosed in U.S. Pat. No. 4,145,412.

This extract is produced by treating a finely cut or ground bloodroot with an organic solvent, such as methanol. The bloodroot is thoroughly stirred with several volumes of the solvent, and is maintained in the solvent for 24 hours or more, at a temperature of about 60° C. Subsequently, the solution is filtered and the methanol is evaporated. The residue is dissolved in chloroform, treated with concentrated hydrochloric acid, filtered and then dried. This dried extract is generally taken up in warm glycerine (65° C.) for mixing with a carrier.

The extract is an excellent breath freshener, tissue conditioner and tooth cleansing agent.

Sanguinarine, a component of sanguinaria extract has also been used as an antiplaque agent and has been demonstrated to be effective in the prevention and control of plaque in U.S. Pat. Appln. Ser. No. 767,606, filed Aug. 20, 1985 now U.S. Pat. No. 4,683,133 which issued July 28, 1987.

However, in mammals with advanced periodontal disease, which is characterized by tissue destruction, high levels of collagenase activity, and alveolar bone resorption, there is a need to provide effective means to control and reverse these conditions.

Periodontal disease accounts for more than 50% of the total tooth mortality in the United States and is the leading threat to oral health in the world, and while limited advances have been made in both prevention and treatment, the essential pathogenesis of the disease is not well understood. Researchers do not doubt that certain microorganisms in oral flora and their metabolic substances constitute the primary extrinsic agents participating in the initiation of periodontal disease.

Recent periodontal ressearch has begun to elucidate the nature of the interaction between these bacterial substances and various host defense mechanisms. Bacterial toxins and antigens have been shown to activate the immune system of the host, causing tissue destruction and alveolar bone resorption, both which are characteristic of periodontal disease. [1,2]

1. Schluger S, Yuocelis NA, Page RC: *Periodontal Disease.* Philadelphia, Lea & Febiger, 1977.
2. Page RC, Schroeder HE: *Periodontitis in Man and Other Animals.* Basel, Switzerland, Karger, 1982.

Also, studies have presented evidence that destruction of connective tissue and alveolar bone resorption are mediated by various proteases and protoglycanases released not only by the invading polymorphonuclear neutrophils and macrophages, but also, and more importantly, by most resident connective tissue cells, such as fibroblasts, osteoblasts, and others. [3,4]

3. Sellers A, Reynolds JJ, Meikle MC: *Biochem J* 171:493, 1978.
4. Heath JK, et al. *Biochem Biophys Acta* 800:301–1984.

When confronted with the bacterial antigen, the inflammatory and noninflammatory cells of the host immune system respond by producing various lymphokines and cytokines, including inerleukin 1, which has been shown to be molecularly identical to osteoclast-activating factor (OAF)[5]. These soluble mediators induce rapid synthesis of destructive enzymes by the host cells and thus appear to play a major role in modulating inflammatory responses. [6]

5. Dewhirst FE, et al., *J. Immunol* 135:2562–2568, 1985.
6. Murphy G, Reynolds JJ; *BioEssays* 2: 55–60, 1985.

The primary manifestation of periodontal disease can be described as a hyper reaction of the host immune system. It is exquisitely indicated in clincal sutdies of patients with immunodeficiency diseases who demonstrate significantly lower levels of periodontal symptons in comparison with age-matched controls. Thus, the characterization of periodontal disease as a hypersensitivity reaction of the host defense mechanism, leading to the destruction of host tissue by host cells, has attracted the attention of many researchers in recent years.

Nevertheless, the preventive measures for periodontal disease have been focused primarily on physically or chemically eradicating bacterial plaque.

The increasing body of evidence suggests that bone resorption is a dynamic and complex chainlike event that invovles osteoclasts as well as various other cell types. [7-9] Although anatomic resorption requires the simultaneous degradation of both mineral and organic matrices during cell-mediated resorption of living bone, the molecular details of this process have not been unraveled. Collagen is the major organic component of bone matrix, and collagenase is the enzyme principally associated with the degradation of collagen under physiologic conditions. This specific neutral protease has been associated with the breakdown of connective tissue in a variety of physiologic and pathologic tissues.

7. Rodan GA, Rodan SB: Expression of the osteoblastic phenotype, In Peck Wa (ed): *Bone and Mineral Research, Annual* 2. Amsterdam, Elsevier, 1984, pp 244–285.
8. Baron R, Vignery A, Horowitz M: Lymphocytes, macrophages and the regulation of bone remodeling. In Peck WA (ed.): *Bone and Mineral Research, Annual* 2 Amsterdam, Elsevier, 1984, pp 175–243.
9. Chambers TJ; The pathobiology of the osteoclast. *J Clin Pathol* 38: 241-252, 1985.

It is an object of the invention to provide means for controlling alveolar bone resorption and limiting the levels of collagenase activity in advanced periodontal disease by orally adminstering certainspecified amounts of sanguinarine and its pseudoethanolate.

SUMMARY OF THE INVENTION

In accordance with the invention sanguinarine and its pseudoethanolate are employed in effective levels to control the ravages of advanced periodontal disease.

DETAILED DESCRIPTION OF THE INVENTION

The examples hereinafter provided will set forth the effects of sanguinarine and is pseudoethanolate on bone resorption in relation to collagenase synthesis.

EXAMPLE I

Bone cultures were prepared according to the method described by A Matsumoto et al in Arch. *Oral Biol.*, 24, 403-405 (1979) using five-day-old mouse calvaria cultures.

The medium consisted of a modified broth culture supplemented with 10% heat-inactivated horse serum with or without heparin (10 U/ml). Bone resorption was stimulated with parathyroid hormone (PTH, 1 U/ml). Highly purified sanguinarine and it pseudoethanolate[a] were dissolved in dimethylsulfoxide (DMSO) and dded to the culture medium (0.1% vol/-vol). The controls received the same amount of DMSO. The medium was renewed every two days, and incubation was continued for four to six days.

a: prepared by dissolving sanguinarine in ethanol and raising the pH with NaOH or NH4 OH to precipitate a solid.

Bone resorption was determined by measuring the levels of calcium concentration in the medium at designated intervals. The concentration of total calcium was mesured by fluorometeric titration with a Corning Mode 940 calcium analyzer as described by Cowen et al in *Biochem Int* 11:273-280, 1985. Each experimental group consisted of four cultures. Bone resorption was expressed either as the concentration of calcium in the medium (mg/dL) or as a percentage of the value induced with PTH.

Collagenase was isolated from harvested medium samples of calvaria cultures (containing heparin) [10] by passing the medium through multiple small columns of heparin-sepharose gel, as illustrated in FIG. 1. Most of the serum components, including collagenase inhibitor, were removed by this affinity chromatography process before collagenase assay.

10. S, Sakamoto et al in Peck WA (ed): *Bone and Mineral Research, Annual* 4 Amsterdam, Elsevier, 1986.

The isolated collagenase was entirely in the latent form (enzymatically inactive) and was activated with 1 mmol/L p-aminophenylmercuric acetate (p-APMA) before assay. Standard assay conditions are also illustrated in FIG. 1.

Sanguinarine and its pseudoethanolate dissolved in DMSO were tested in the collagenase assay using highly purified mouse bone collagenase (active form) prepared as described S. Sakamoto et al in *Arch Biochem Biophys* 188:438-449, 1978.

Figure 2:
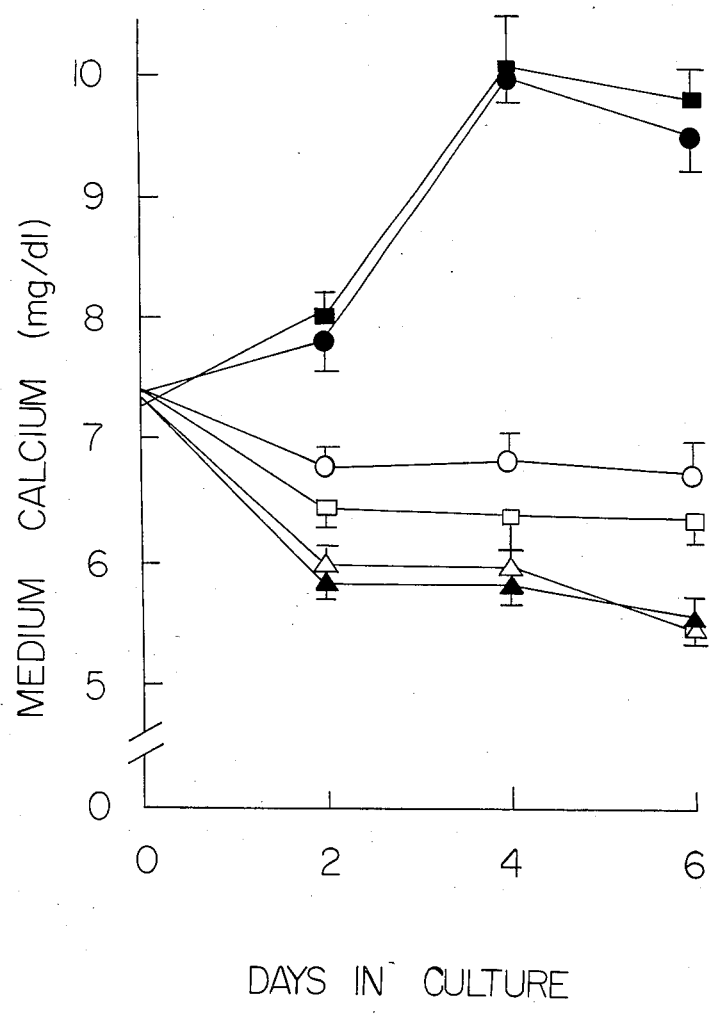
Figure 3:
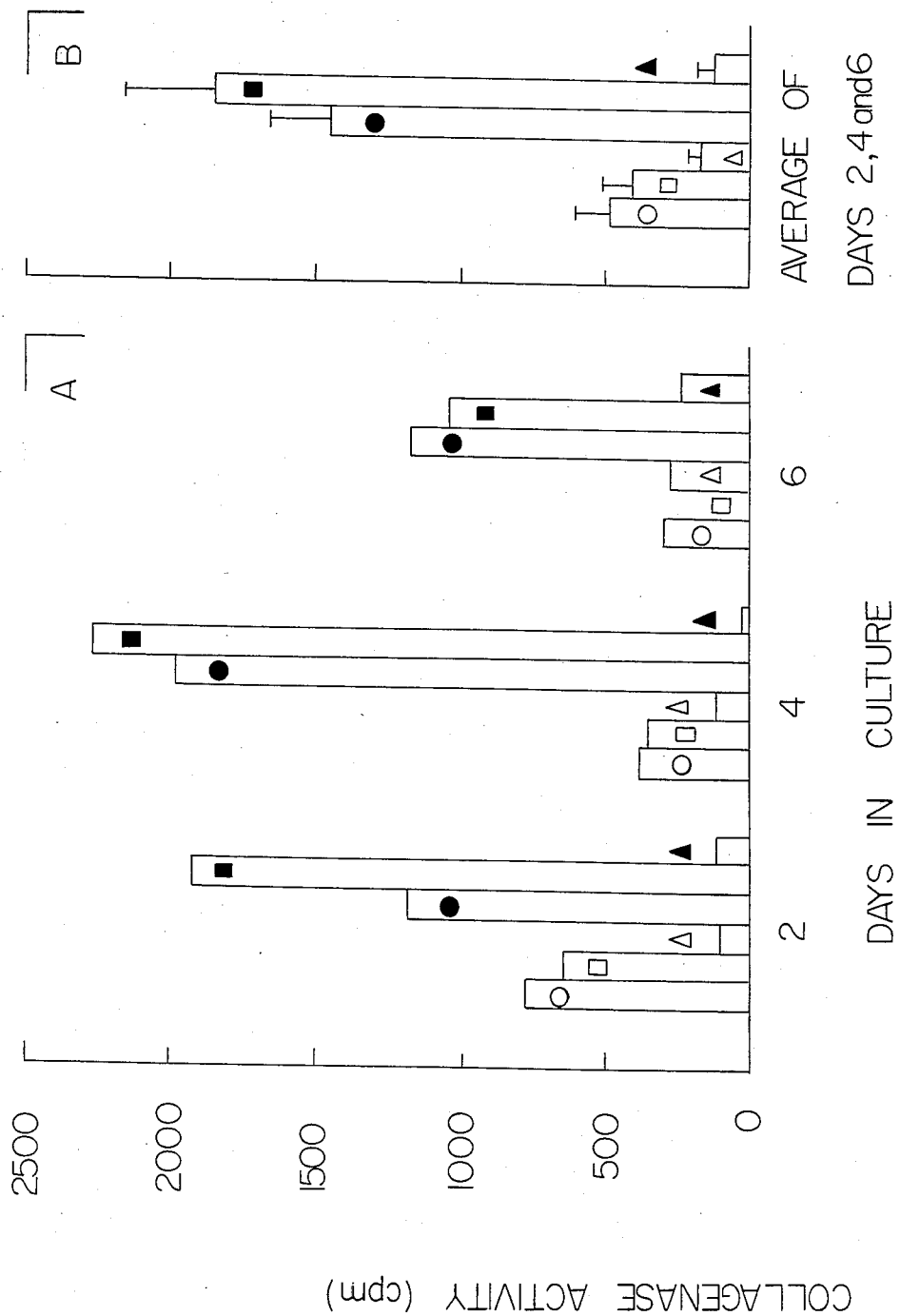

To test the effects of sanguinarine on mouse calvaria with respect to bone resorption (stimulated by PTH) and collagenase release from bone explants, changes in calcium concentrations and collagenase levels were analyzed in media during the culture period. FIG. 2 shows that at two, four and six days in culture, the PTH-treated group had high levels of bone resorption. Both PTH and control treated with 20 umol/L sanguinarine had lower vlaues than controls not treated with sanguinarine, indicating that 20 umol/L of sanguinarine completely inhibited PTH-stimulated bone resorption. FIG. 3 shows activity levels for collagenase released by bone explants in the same culture experiment presented in FIG. 2.

All PTH groups exhibited high levels of collagenase activity throughout the culture period, but the PTH group containing CMSO was slightly higher than the PTH group without DMSO, and the PTH group treated with 20 umol/L sanguinarine had even lower values than the various controls, indicating the sanguinarine blocks the release of collagenase from bone explants.

Figure 4:
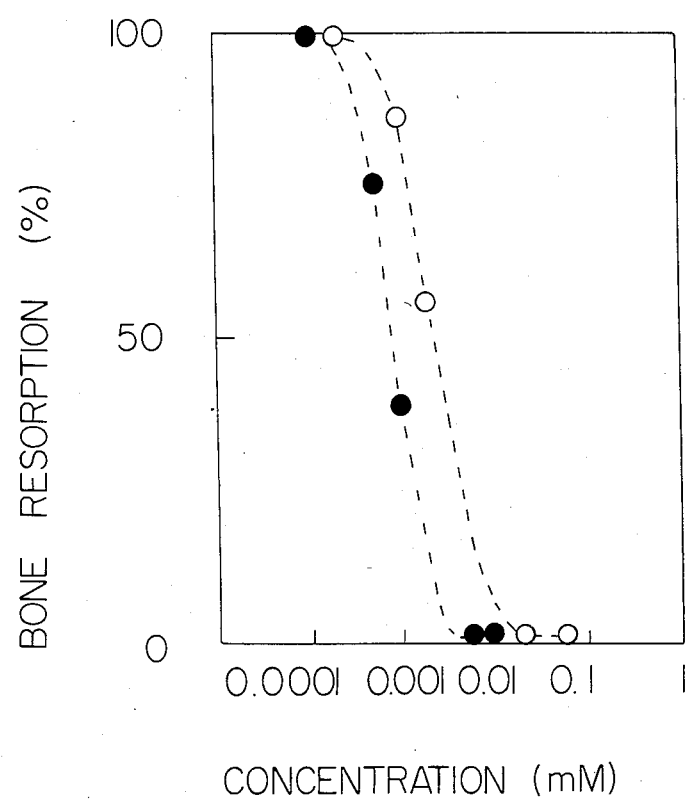

Collagenase levels in the media generally correlated well with the extent of bone resorption among culture groups (FIGS. 2 and 3). Sanguinarine pseudoethanolate at 5 umol/L also completely inhibited bone resorption (FIG. 4) and blocked collagenase release from bone explants. FIG. 4 shows the effects of sanguinarine and its pseudoethanolate on PTH stimulated bone resorption at various concentrations. The effective concentration ragnes of sanguinarine and its pseudoethanolate were approximately 1 to 20 umol/L and 0.2 to 5 umol/L respectively.

Sanguinarine pseudoethanolate appeared to be approximately five to ten times more potent than sanguinarine in the present culture system.

Figure 5:
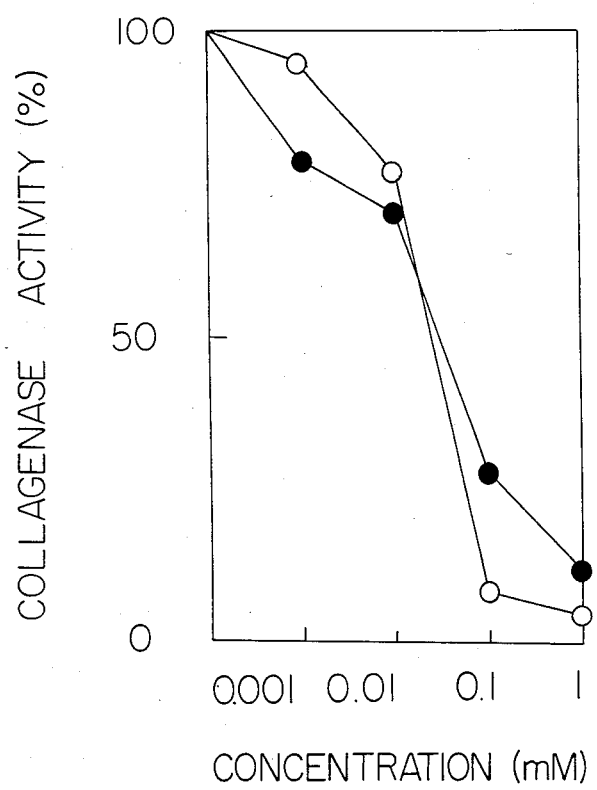

The direct effect of sanguinarine on colagenase activity was also tested in the collagenase assay. FIG. 5 shows that both sanguinarine and the pseudoethanolate form inhibited the active form of purified mouse bone collagenase, but at 10 to 100 times the concentrations required in the culture system (FIG. 4). Sanguinarine pseudoethanolate was more inhibitory than sanguinarine at lower concentrations, but the effect was reversed at higher concentrations. When sanguinarine pseudoethanolate was added to the collagenase assay mixture (pH 7.5), the color turned to orange, indicating that the ethanolate was being rapidly converted to sanguinarine.

It is clear that sanguinarine affected mouse calvaria and inhibited both collagenase release and bone resorption, and the results indicate a role for collagenase secreted by bone explants in the extracellular degradation of bone matrix collagen during bone resorption.

Sanguinarine pseudoethanolate was approximately five to ten times more potent than sanguinarine with respect to inhibitation of bone resorption (FIG. 4), and indicates that the thanolate penetrates the membrane more easily because of its lipophilic character.

Higher concentrations of sanguinarine were required for direct inhibition of collagenase activity (FIG. 5).

while 5 umol/L sanguinarine pseudoethanolate (1.75 ug/mL) is the preferred amount required to inhibit bone resorption in the present study (FIG. 4), a range of from about 0.2 to about 10 umol/L have been found to be effective to inhibit bone resorption and collagenase release due to parathyroid hormone stimulation.

In the case of sanguinarine per se, about 10 umol/L is the preferred amount to inhibit bone resorption and collagenase release due to parathyroid hormone stimulation; however, it has been found that a range of from about 1 to 20 umol/L will work in the context of the invention.

It is understood that the foregoing detailed description is by way of illustration only, and that variations can be made within the invention scope without departing from the spirit of the invention.

What is claimed is:

1. A method of inhibiting bone resorption and collagenase activity in mammals having periodontal disease, comprising adminstering to said mammals in amount from about 0.2 to about 20 umol/L of sanguinarine, sanguinarine pseudoethanolate or mixtures thereof dissolved in dimethylsulfoxide.

2. The method of claim 1 wherein said sanguinarine is administered in amounts from about 1 to about 20 umol/L.

3. The method of claim 1 wherein sanguinarine pseudoethanolate is administered in amounts from about 0.2 to about 20 umol/L.

4. The method of claim 2 wherein sanguinarine is administered in amount of 20 umol/L.

5. The method of claim 4 wherein sanguinarine pseudoethanolate is administered in amounts of 5 umol/L.

* * * * *